(12) United States Patent
Hillebrand et al.

(10) Patent No.: US 6,699,987 B2
(45) Date of Patent: Mar. 2, 2004

(54) FORMULATIONS AND METHOD FOR ISOLATING NUCLEIC ACIDS FROM OPTIONAL COMPLEX STARTING MATERIAL AND SUBSEQUENT COMPLEX GENE ANALYTICS

(75) Inventors: Timo Hillebrand, Berlin (DE); Peter Bendzko, Berlin (DE)

(73) Assignee: Invitek Gesellschaft fur Biotechnik & Biodesign mbH, Berlin (DE)

(*) Notice: Subject to any disclaimer, the term of this patent is extended or adjusted under 35 U.S.C. 154(b) by 0 days.

(21) Appl. No.: 09/454,740

(22) Filed: Dec. 6, 1999

(65) Prior Publication Data

US 2001/0041332 A1 Nov. 15, 2001

(30) Foreign Application Priority Data

Dec. 4, 1998 (DE) .......................... 198 56 064

(51) Int. Cl.[7] .................. C07H 21/00; C07H 21/02; C07H 21/04; C12P 19/34; G01N 1/18
(52) U.S. Cl. ............... 536/25.4; 536/25.41; 536/23.1; 435/91.3; 435/91.32; 436/177
(58) Field of Search .................. 435/6, 5; 536/23.1, 536/24.3; 935/77, 78

(56) References Cited

U.S. PATENT DOCUMENTS

| | | | |
|---|---|---|---|
| 5,438,127 A | | 8/1995 | Woodard .................. 536/25.4 |
| 5,503,816 A | | 4/1996 | Woodard .................. 423/304 |
| 5,523,392 A | | 6/1996 | Woodard .................. 536/25.4 |
| 5,552,325 A | * | 9/1996 | Nochumson et al. ....... 436/177 |
| 5,606,046 A | | 2/1997 | Woodard .................. 536/25.4 |
| 5,610,291 A | | 3/1997 | Woodard .................. 536/25.4 |
| 5,616,701 A | | 4/1997 | Woodard .................. 536/25.4 |
| 5,650,506 A | * | 7/1997 | Woodard et al. ........... 536/25.4 |
| 5,674,997 A | | 10/1997 | Woodard .................. 536/25.4 |
| 5,824,517 A | * | 10/1998 | Cleuziat et al. ........... 435/91.2 |
| 5,858,649 A | * | 1/1999 | Asgari et al. ................. 435/5 |
| 5,907,085 A | * | 5/1999 | Gonsalves et al. .......... 800/205 |
| 5,948,656 A | * | 9/1999 | Anderson et al. .......... 435/183 |
| 5,973,137 A | * | 10/1999 | Heath ....................... 536/25.4 |
| 6,060,246 A | * | 5/2000 | Summerton et al. ........... 435/6 |

FOREIGN PATENT DOCUMENTS

| | | |
|---|---|---|
| DE | 4139664 | 6/1993 |
| WO | 9534569 | 12/1995 |

OTHER PUBLICATIONS

B. Vogelstein et al.; Preparative and Analytical Purification of DNA from Agarose; Proc. Natl. Acad. Sci., USA, vol. 76, No. 2, Feb. 1979, pp. 615–619.

M. Marko et al.; A Procedure for the Large–Scale Isolation of Highly Purified Plasmid DNA Using Alkaline Extraction and Binding to Glass Powder; Analytical Biochemistry 121, 1982, pp. 382–387.

J. Sambrook et al. , ; Molecular Cloning, A Laboratory Manual; Cold Spring Harbor Laboratory Press, 1989, (cover page of standard book).

* cited by examiner

*Primary Examiner*—Gary Benzion
*Assistant Examiner*—Arun Kron Chakrabarti
(74) *Attorney, Agent, or Firm*—Norris McLaughlin & Marcus

(57) ABSTRACT

The subject of the invention are formulations not containing chaotropic components for isolating nucleic acids with binding to a solid phase, in particular of DNA, from optional complex starting materials and quantities containing a lysis/binding buffer system which comprises at least one antichaotropic salt component, a solid phase and wash and elution buffers known as such. The lysis/binding buffer system may be an aqueous solution or a solid formulation in reaction vessels ready for use. All carriers used for isolation by means of chaotropic reagents, preferably glass fiber mats, glass membranes, silica carriers, ceramics, zeolites or materials showing negatively functionalised surfaces or chemically modified surfaces which may be converted to a negative charge potential may serve as a solid phase.

Figure 1:
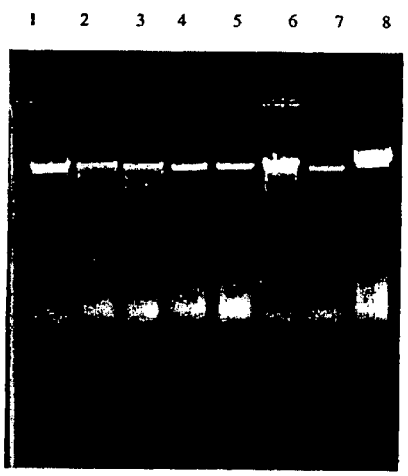

Furthermore, the subject of the invention is a method for isolating nucleic acids, in particular DNA, from optional complex starting materials with using the formulations according to the invention which is characterized by the lysis of the starting material, binding of nucleic acids to a carrier, washing of the nucleic acids bound to the carrier and elution of nucleic acids.

17 Claims, 10 Drawing Sheets

Traces
1 - onion (fresh)
2 - chive (fresh; green)
3 - chive (fresh; green)
4 - geranium (hanging; flowers and leaves; fresh)
5.- geranium (standing; leaves; fresh)
6 - yew (needles; fresh)
7 - mousetail grass (fresh; leaves; green)
8 - common tansy (fresh; green, leaves)

1 2 3 4 5 6 7 8 9 10

Traces

1 - whole blood; frozen; 50 ul
2 - whole blood, 100 ul
3 - cucumber; 50 mg
4 - tomoto plant leaf; 100 mg.
5 - saliva sample; 100 ul
6 - chicken liver; foodstuffs frozen; 5 mg.
7 - chicken liver, foodstuffs; frozen; 20 mg.
8 - hair roots
9 - turkey salami; 50 mg.
10 - yew, needles, 100 mg.

Traces 1 - 6: DNA from swab samples of oral mucosa

Traces:

1 - 10:  Extraction method according to the invention
11 - 20: Comparative method Traces:

1 - 4: Extraction method according to the invention
5 - 8: Comparative method

Figure 6

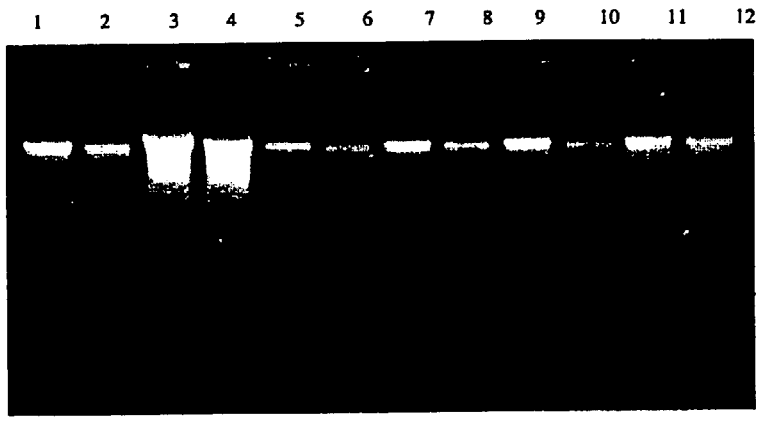

Traces:

1: Extraction method according to the invention; 5 mg kidney
2: Comparative method; 5 mg kidney
3: Extraction method according to the invention; 20 mg. kidney
4: Comparative method: 20 mg kidney
5: Extraction method according to the invention; 5 mg heart
6: Comparation method; 5 mg heart
7: Extraction method according to the invention; 20 mg heart
8: Comparative method; 20 mg heart
9: Extraction method according to the invention; 5 mg liver
10: Comparative method; 5 mg liver
11: Extraction method according to the invention; 20 mg liver
12: Comparative method; 20 mg. liver

Figure 7

|  1   2   3   4   5   6   7   8   9   10 |

Traces:

1/2: Membrane supplier A (commercially available extraction kit)
3/4: Membrane supplier B (commercially available extraction kit)
5/6: Membrane supplier C (commercially available extraction kit)
7/8: Carrier suspension of silicon oxide
9/10: Carrier suspension of diatom earth
11/12: Carrier suspension of aerosiles (200 $m^2/g$)

Traces:

1-4: DNA extracted from saliva samples
5-6: DNA extracted from whole blood
7-8: DNA extracted from deparaffined tissue material COO microtest plate strips unmodified microtest plats strip

FORMULATIONS AND METHOD FOR ISOLATING NUCLEIC ACIDS FROM OPTIONAL COMPLEX STARTING MATERIAL AND SUBSEQUENT COMPLEX GENE ANALYTICS

Subject of the invention are formulations which do not contain chaotropic components for isolating nucleic acids with binding them to a solid phase, in particular DNA, from optional complex starting materials and quantities which contain a lysis/binding buffer system involving at least one antichaotropic salt component, a solid phase and wash and elution buffers known as such. The lysis/binding buffer system may be present as an aqueous solution or as a solid formulation of reaction vessels ready for use. All carriers applied for isolation by means of chaotropic reagents, preferably glass fiber mats, glass membranes, silicon carriers, ceramics, zeolites or materials possessing negatively functionalised or chemically modified surfaces which may be converted to a negative charge potential, may serve as a solid phase.

Furthermore, the subject of the invention is a method for isolating nucleic acids, in particular DNA, from optional complex starting materials with using the formulations according to the invention which is characterized by the lysis of the starting material, binding of nucleic acids to a carrier, washing of the nucleic acids bound to the carrier and elution of the nucleic acids, with amplifying selected sequence sections subsequently, if necessary, and analyzing the multiplied gene sections in the very same reaction cavity subsequently, if necessary. Fields of application of the methods are all laboratories dealing with DNA isolation such as forensic medicine, food diagnostics, medical diagnostics, molecular biology, biochemistry, genetic engineering and all other adjacent fields.

Given classical conditions, DNA are isolated from cells and tissues by decomposing the starting materials which contain nucleic acids under strongly denaturating and reducing conditions, with partly also using protein-degrading enzymes, purifying the escaping nucleic acid fractions in phenol/chloroform extraction steps and obtaining nucleic acids by means of dialysis or ethanol precipitation from the aqueous phase (Sambrook, J.; Fritsch, E. F.; and Maniatis, T., 1989, CSH, "Molecular Cloning").

The "classical methods" for isolating nucleic acids from cells and, in particular, from tissues, are very time-consuming (partly more than 48 hours), require a remarkable expenditure on apparatuses and, apart from that, are not implementable under field conditions. In addition, such methods are due to the used chemicals phenol and chloroform, to a not insignificant degree, dangerous to health.

Various alternative methods for isolating nucleic acids from various biological starting materials allow to avoid the expensive and unhealthy phenol/chloroform extraction of nucleic acids and a reduction of the expenditure of time.

All these methods are based on a method for the preparative and analytical purification of DNA fragments from agarose gels developed by Vogelstein and Gillespie (Proc. Natl. Acad. Sc. USA, 1979, 76, 615–619). The method combines the dissolution of agarose containing the DNA bands to be isolated in a saturated solution of a chaotropic salt (NaJ) with binding DNA to glass particles. The DNA fixed on the glass particles is subsequently washed with a wash solution (20 mM of tris HCl [pH 7.2]; 200 mM of NaCl; 2 mM of EDTA; 50% v/v ethanol) and thereupon dissolved from the carrier particles.

Till the present day this method has been a few times modified and is, for the time being, applied for various processes of extraction and purification of nucleic acids of various origin (Marko, M. A.; Chipperfield, R. and Bimboim, H. G.; 1982, Anal. Biochem., 121, 382–387).

In addition, today exists worldwide also a multitude of reagent systems primarily for purifying DNA fragments of agarose gels and for isolating plasmide DNA from bacterial lysates, yet also for isolating nucleic acids with longer chains (genomic DNA, cellular total RNA) from blood, tissue or also cell cultures.

All these commercially available kits are based on the principle of binding nucleic acids to mineral carrier in the presence of solutions of various chaotropic salts, which is sufficiently known, and use suspensions of finely grinded glass powder as carriers (e.g. glass milk, BIO 101, La Jolla, Calif.), diatom earths (company Sigma) or also silica gels (Diagen, Del. 41 39 664 A1).

A method for isolating nucleic acids practicable for a multitude of various uses is represented in U.S. Pat. No. 5.234.809 (Boom). There, a method for isolating nucleic acids from starting materials which contain nucleic acids by incubating the starting materials with a chaotropic buffer and a solid phase binding DNA is described. The chaotropic buffers implement the lysis of the starting materials as well as binding of nucleic acids to the solid phase. The method is well suited for isolating nucleic acids from small quantities of materials, being in practice especially applied in the field of isolating viral nucleic acids.

Specific modifications of these methods relate to the use of novel carriers which show advantages in application as to specific aspects (Invitek GmbH WO-A 95/34569).

Yet, decisive drawbacks of the method of isolating nucleic acids from complex starting materials on the basis of incubating the starting material with a chaotropic buffer and a solid phase consist a.o. in the fact that the decomposition of cells to be brought about by the chaotropic buffers is not applicable to all materials or works only extremely insufficiently and with a high expenditure of time also for bigger quantities of starting materials. Apart from that, mechanic homogenisation methods are required if e.g. DNA has to be isolated from tissue samples. Furthermore, various concentrations of different chaotropic buffers have to be always used for investigating various aspects. Thus, the method is, in no way, universally applicable.

Though problems arising due to a possibly difficult lysis of the starting material may be solved by a number of commercially available products for isolating nucleic acids (especially for isolating genomic DNA from complex starting materials), they have the big drawback that no longer a classical "single tube" method is concerned which characterizes the method according to the U.S. patent as the lysis of the starting material is carried out in a usual buffer including a proteolytic enzyme. The chaotropic ions required for the subsequent binding of nucleic acids e.g. to centrifugation membranes have to be added separately to the lysis batch after completing the lysis. But they cannot form part of the lysis buffer as the protein destroying function of chaotropic salts is known and would, of course, immediately destroy the proteolytic enzyme required for an efficient lysis.

That is why the methods of isolating nucleic acids with using chaotropic salts have gained acceptance worldwide in spite of a number of drawbacks and are used a million times by means of commercially available products. These systems are extremely simple to apply and follow always the principle of lysis of starting materials, the subsequent binding of nucleic acid to the solid phase of a glass or silica membrane which is in a centrifugation column on a carrier suspension, washing of the bound nucleic acids and the subsequent elution of the nucleic acids with a buffer of an insignificant ionic strength.

All these systems are based on binding the nucleic acids to the respective carrier surfaces in the presence of chaotropic salts, i.e. at least one buffer solution contains a chaotropic salt as main component. This refers possibly already to the lysis buffer or in the case of systems including proteolytic enzymes a required binding buffer which is added after completing the lysis of the starting material.

The series of Hofmeister for salting out negatively charged, neutral or basic protein solutions form the basis for chaotropic salts. Thus, chaotropic salts are characterized by denaturing proteins, increasing the solubility of nonpolar substances in water and destroying hydrophobic interactions. According to the state of the art notably these properties, also with buffer systems of chaotropic salts, destroy the superior structure of the aqueous medium to thus bring about the binding of the nucleic acids to selected solid phases. The most important agents for isolating nucleic acid are sodium perchlorate, sodium iodide, potassium iodide, guanidine thiocyanate and guanidine hydrochloride. Yet, on the one hand, they are expensive and, on the other hand, and partly toxic or corrosive.

Till the present day a very great number of patent applications and granted patents have been based on this state of the art, where always variants of the method are concerned such as e.g. the use of new carriers or more efficient wash buffers etc. with the basic principle being always the use of chaotropic salts for binding to a solid phase which consists of silica materials.

The physical-chemical principle of binding nucleic acids to mineral carriers in the presence of chaotropic salts is regarded to be acknowledged among international experts. Binding of nucleic acids to the surfaces of the mineral carrier consists in the disturbance of superior structures of the aqueous medium through which nucleic acids are adsorbed to the surface of mineral materials, in particular glass or silica particles. Disturbing the superior structures of the aqueous medium requires always the presence of chaotropic ions. In case of high concentrations of chaotropic salts the reaction proceeds nearly quantitatively. Owing to these physical-chemical findings described experts proceed on the fact that all commercially available systems for isolating nucleic acids have to contain buffer compositions with a high ionic strength of the chaotropic salts for binding nucleic acids to a solid phase binding nucleic acids.

The more surprising were the findings according to the invention that formulations containing antichaotropic salts in a lysis/binding buffer system are equally and better suited for isolating nucleic acids from optional, in particular complex starting materials.

The invention is implemented according to the claims. That is why the subject of the invention are formulations and methods which do not contain chaotropic components for isolating nucleic acids with binding them to a solid phase, in particular DNA, from optional complex starting materials which contain a lysis/binding buffer system involving at least one antichaotropic salt component, a solid phase and wash and elution buffers known as such. Antichaotropic components in the sense of the invention are ammonium, caesium, sodium and/or potassium salts, preferably ammonium chloride.

In addition, the lysis/buffer system contains detergents known as such and additives such as e.g. tris-HCL, EDTA, polyvinyl pyrrolidone, CTAB, triton X-100, N-lauryl sarcosine, sodium citrate, DTT, SDS and/or Tween. In a preferred variant of execution the lysis/binding buffer system contains an alcohol such as e.g. ethanol and isopropanol and enzymes, if necessary, preferably enzymes degrading protein, e.g. proteinase, for binding to the solid phase. With the invention the principle corresponding to the state of the art may be used to solve a specific problem of isolating nucleic acid or to optimize and make efficient an existing variant as regards specific relevant parameters. Thus it is suited for being applied as a fully automatic high-throughput method.

Completely unexpected and unlike the known state of the art, nucleic acids, in particular genomic DNA, may be bound according to the present invention to a mineral supporting agent with lysis/binding buffer systems not containing chaotropic salt components and also eluted under the usual conditions.

Furthermore it was stated that a multitude of completely different salts as components of lysis/binding buffer systems also usual as such, if necessary, are sufficient for binding nucleic acids to classical carriers on the basis of glass or silica.

To our particular surprise, the best results may be achieved with salts showing after their chemical-physical characteristics the absolutely opposite effects with regard to the chaotropic salts used so far for binding nucleic acids. Thus, we may call these salts antichaotropic.

Thus, it was possible to achieve at least the same quantitative and qualitative results in extractions of genomic DNA from various complex starting materials (e.g. blood, tissue, plants) with lysis/binding buffers the main component of which were e.g. ammonium salts instead of chaotropic salts (commercial extraction kits), keeping the other reaction components, carriers usual so far constant and given completely the same reaction course.

Thereby, notably the ammonium ion is the ion in the Hofmeister series showing in chemical-physical respect properties which are absolutely opposite to the known chaotropic ions of this series.

Solely by replacing the chaotropic salt component so far used by an antichaotropic salt component in the lysis/binding buffer, with all other parameters being constant, on the surfaces of the solid carriers known as such an at least adequate quantitative isolation of nucleic acids is possible.

That means that it is in the same way possible to isolate nucleic acids also from complex starting materials by a salt not denaturating proteins but stabilizing them which does not increase the solubility of nonpolar substances in water but reduces it and which does not destroy hydrophobic interactions but intensifies them, to purify and supply them to applications usual as such.

With the present invention a novel, alternative mechanism for binding nucleic acids to solid, preferably mineral carriers, and on this basis, a universally applicable novel method for isolating nucleic acids from complex starting materials is provided.

Thus, the invention allows to use an alternative chemism as essential component of the respective test kits (formulations) through the use of novel compositions of lysis/binding buffers on the basis of chaotropic salts for isolating nucleic acids, especially for isolating genomic DNA based on binding the nucleic acids to the various solid phases of silica or glass materials usual as such.

Thereby, the method according to the invention using antichaotropic salts follows the process courses for isolating nucleic acid known from the laboratory routine practice and is characterized by:

1. Lysis of starting material
2. Binding of nucleic acids to a solid phase (centrifugation column or suspension)
3. Washing of the bound nucleic acids
4. Elution of the nucleic acids with a low-salt buffer known as such.

The invention allows a highly efficient and fast isolation of nucleic acids, especially genomic DNA from an optional and, if necessary, complex starting material. The antichaotropic ions required for binding may be a component of the lysis/binding buffer even when including proteolytic enzymes. The method according to the invention is thus easily and universally applicable.

The isolation of nucleic acids, in particular DNA, from optional starting materials is effected by incubation of the starting materials containing the nucleic acid without using chaotropic substances which are brought into contact with the lysis/binding buffer system which comprises an aqueous solution containing an antichaotropic salt component, at least a detergent, if necessary, additives and, if necessary, an enzyme, and an optional solid phase, preferably glass fiber mats, glass membranes, glasses, zeolites, ceramics and other silica carriers thus bringing about the lysis of the starting material and the subsequent binding of DNA to the solid phase. Subsequently, the bound nucleic acid is washed according to methods known as such and dissolved from the solid phase.

In case of special extraction protocols an additional detergent, an alcohol or a detergent/alcohol mixture may be added to the lysis batch, if necessary.

Preferred starting materials are compact plant materials such as e.g. fruit, seeds, leaves, needles etc., clinically relevant samples such as whole blood, tissue, microbioptates, paraffin-coated materials, ercp-samples, swabs, foodstuffs such as e.g. fish, sausage, tins, milk, forensic samples such as e.g. hair roots, cigarette butts, blood stains and other samples containing DNA.

Preferred ions in the sense of the invention are the antichaotropic ammonium ions represented in the Hofmeister series, caesium ions and potassium and sodium ions or combinations of these ions, preferably ammonium chloride. They are used in an ionic strength of 0.1 to 8 M for lysis/binding.

For binding nucleic acids, in particular DNA, to the solid carriers already low concentrations of these salts of preferably $\leq 1$ M will be sufficient, in certain applications preferably even concentrations of $\leq 0.5$ M with higher ionic concentrations being successful in the quantitative isolation of nucleic acids from bigger quantities of starting materials.

By using antichaotropic salts which have a protein stabilizing effect as essential components of a lysis buffer in a preferred form of execution of the invention also proteolytic enzymes such as e.g. proteinase K may be added for supporting and making the lysis process more effective, thus also antichaotropic salts of a high ionic strength as e.g. 5 M are added for the required decomposition of cells, thus allowing a quantitative isolation of nucleic acids.

Buffer systems of the state of the art with the known chaotropic salts may not contain proteolytic enzymes of the required high ionic strength as it is, in general, necessary for a quantitative isolation of nucleic acids. Thus, they have always to be subsequently added for binding nucleic acids to the solid phases.

In the lysis buffers/binding buffers according to the invention preferably anionic, cationic or neutral proteolytic enzymes such as e.g. SDS, triton X-100, Tween or CTAB are used as detergents.

After completing the lysis of the starting material the suspension is separated from the components not yet completely lysed in a short centrifugation step, if necessary, and directly incubated with the material binding DNA or, as already described, after adding an additional detergent, alcohol or a detergent/alcohol mixture incubated with the solid phase. In the lysis buffer system there are possibly additional insignificant concentrations (<50 mM) of EDTA and/or tris-HCl. For isolating DNA from very strongly polluted starting materials preferably also 2–4% polyvinyl pyrrolidone or other known substances are added to the buffer system to bind inhibitory components selectively.

For instance commercially available glass fiber mats in centrifugation columns, silicone compounds such as $SiO_2$ of a various particle size have proved to be remarkable as binding material for the DNA to be isolated. Thus, all the materials used for isolating nucleic acids by means of chaotropic buffers may be used.

After incubation with the DNA binding material the lysate is separated from the binding material by a short centrifugation step. Subsequently, it is washed with a wash buffer e.g. consisting of at least 50% ethanol and a low salt concentration, if necessary, e.g. NaCl, in a way known as such, the carrier is dried and the bound DNA is eluted by means of a low salt buffer (tris-HCl; TE; water) known as such and at a preferable temperature of 50–70° C.

A further variant of applying the invention consists in adding proteolytic enzymes, preferably proteinases such as e.g. proteinase K, for the lysis of starting materials which are difficult to decompose, e.g. compact tissue samples, hair roots or for optimizing the efficiency of lysis and reducing the required lysis periods.

Thus, the invention allows to apply universally applicable methods of isolating nucleic acids, in particular DNA, from all starting materials containing DNA as well as from optional quantities of most various starting materials in novel combinations of antichaotropic salts as essential components of lysis buffer mixtures, with all carriers so far used and their variants being equally efficiently used and the regulations governing the isolation of nucleic acids which have been so far applied being identically usable.

In its most general variant of application by means of the method according to the invention an extraction of nucleic acid from all selected complex starting materials corresponding to the state of the art, i.e. by means of the new universal buffer system, the highly efficient lysis and subsequent binding of nucleic acid to a mineral carrier from compact plant materials (e.g. fruit, seeds, leaves, needles etc.), from clinically relevant samples (e.g. whole blood, tissue, microbioptate, paraffin-coated materials, ercp-samples, swabs), from foodstuffs (e.g. fish, sausage, tins, milk), from forensic samples (e.g. hair roots, cigarette butts, blood stains) as well as from other starting materials may be carried out successfully, extremely easiliy and very quickly.

A further advantage of the method consists in the fact that it allows to isolate DNA highly efficiently from an extremely small quantity of starting materials (e.g. isolation of DNA from 1 $\mu$l of whole blood, hair roots, microbiopsy<1 mg) as well as from very big quantities of starting materials such as e.g. 50 ml of whole blood, 1 g of tissue material, <1 g of plant material.

So Further advantages of replacing chaotropic salts by antichaotropic salts consist in the fact that the buffers used have no longer toxic or corrosive effects owing to chaotropic chemicals lacking.

Apart from a most general variant of execution optimizations of the extraction method related to specific applications allow to isolate nearly quantitatively the DNA quantities contained in the starting sample. It is astonishing that higher DNA yields may be obtained by means of the method according to the invention without using chaotropic ions of a high concentration binding DNA according to the state of the art than this has been possible so far by means of commercially available and highly optimized extraction kits.

A selection of the respective comparative results achieved by means of commercially available extraction kits is represented in the examples of execution. These results demonstrate clearly the potentials of the invention.

Apart from isolating DNA from all complex starting materials which contain DNA a further variant of applying the method according to the invention allows to isolate highly efficiently plasmide DNA from bacterial lysates and without using chaotropic salts as such required for binding plasmide DNA to mineral carriers according to the state of the art. Thus, in accordance with the process steps of isolating plasmide DNA by means of basic lysis known to the expert the required so-called neutralization reaction is carried out by means of the classical solution III (Maniatis and Sambroek) and this solution III in a thus existing dual function implements also simultaneously the binding of the plasmide DNA to the solid carriers customary as such. Thus, the usual addition of a chaotropic guanidinium hydrochloride is not required for binding the plasmide DNA.

The bound plasmide DNA is also washed in a way known as such and eluted from the carrier. The method is suited for isolating plasmide DNA from all starting quantities used (mini to giga). Thereby, the plasmide DNA yields obtained are identical with the yields isolated according to traditional, commercially available methods. However, the method according to the invention is much more moderate in price than all other systems known as chaotropic salts are very cost-intensive.

Thus, the method using antichaotropic salts is excellently suited for designing automatable systems for isolating plasmide where the price/preparations are a decisive criterion of selection, as is known.

The formulations according to invention allow in a surprising way the access to further, highly interesting and novel applications in the field of isolating nucleic acids and of diagnostics.

In a further form of applying the invention the present new lysis/binding buffer systems containing at least one antichaotropic salt component are in a position to bind nucleic acids to solid phases which have a negatively charged surface or surfaces which have a negative charge potential.

Methods and means of purifying nucleic acids with the binding of nucleic acid being effected to chemically modified solid phases are known from the state of the art (U.S. Pat. No. 5,523,392; Purification of DNA on Aluminium Silicates and Phosphosilicates; U.S. Pat. No. 5.503.816; Silicate Compounds for DNA Purification; U.S. Pat. No. 5,674,997; DNA purification on modified Silicates; U.S. Pat. No. 5,438,127; DNA Purification by solid phase extraction using a $PCl_3$ modified glass fiber membrane; U.S. Pat. No. 5,606,046: DNA purification by solid phase extraction using trifluorimetric acid washed glass fiber membrane; United States Patent: DNA purification by solid phase extraction using glass fiber membrane previously treated with trifluoroacetic acid and then with fluoride ion, hydroxide ion, or $BCl_3$, U.S. Pat. No. 5,610,291: Glass fiber membranes modified by treatment with $SiCl_3$, $AlCl_3$ or $BCl_3$ and washing with NaOH to set as a DNA adsorbant; U.S. Pat. No. 5,616,701: DNA purification by solid phase extraction using hydroxide-washed glass fiber membrane; U.S. Pat. No. 5.650.506: Modified glass fiber membranes useful for DNA purification by solid phase extraction).

Thereby, the prerequisite for this binding of nucleic acid is always that the membranes used for the binding are doped with positive ionic charges by chemical modification reactions. Thus, it is obvious that a binding will be brought about by a Coulomb interaction between the positively charged surface of the membranes used and the negative ionic charge of the phosphate bone of nucleic acids. Thus, the principle of binding nucleic acids to positively charged solid phases already for many years has been a standard application, e.g. for DNA/RNA blotting techniques on positively charged nylon filters, as is known, which is sufficiently known among experts.

Yet, a completely essential drawback of this method described is that it is not suited for isolating nucleic acids, i.e. it is completely impossible to isolate nucleic acids from complex starting materials. Starting material are always already isolated nucleic acids which have to be isolated in the way known as such as has been shown in the U.S. patent specifications cited. In particular, one aspect does not yet seem to be clear to the expert, thereby. The binding conditions (binding under physiological buffer conditions) described and the elution conditions are identical. There is not to be seen how the nucleic acids may be again dissolved from the membrane given the same buffer conditions for binding the nucleic acids to the positively charged membrane.

Finally, the represented means and the respective method may be practically applied only in a very narrow way. Binding of synthetically produced oligonucleotides to positive surfaces is also known. This is, on its turn, effected by utilizing the Coulomb interactions, i.e. on the basis of linking positive and negative charges, e.g. through modified oligonucleotides (linkage with amino linkers or phosphate linkers). These variants do not allow either an isolation of nucleic acids from complex starting materials.

As has been explained in detail there exist alternative forms of binding nucleic acid for punrying membranes with a sufficient positive charge which do not represent methods for isolating nucleic acids. Binding of nucleic acids is brought about by Coulomb forces based on the interactions between positive ionic charges of the membranes and negative ionic charges of the nucleic acid bone. Thus, this principle seems to be logically explainable.

Based on the isolation of nucleic acids from complex starting materials with antichaotropic salts according to the invention a surprising phenomenon was detected. Thus, it became evident that also negatively charged surfaces or surfaces which may be converted to a negative charge potential are suited for binding nucleic acids using the lysis/binding buffer systems according to the invention. In general, we could not expect such a possibility as not a binding but a repulsion would have to occur owing to equal charge potentials.

The negatively functionalised surfaces or surfaces with potentially negative modifications according to the invention are produced according to methods known as such. The photochemical coupling of an acetyl group, carboxyl group or hyxdroxyl group with the surface of a reaction vessel has e.g. proved to be suited.

The present variant opens up completely new prospects for a complex nucleic acid analytics. Namely, there became obvious that the nucleic acid need not be already isolated for binding to negative or potentially negative surfaces as in all variants described so far. Binding will be effected from the lysis reaction batch, i.e. the starting sample containing the nucleic acid will be lysed and the released nucleic acids will be bound to the negatively charged surface (e.g. a microtest plate cavity or an Eppendorf reaction vessel).

The variant according to the invention allows now to apply completely novel "single tube" and one step methods for isolating nucleic acids from complex starting materials. Such methods provide immense advantages in their application spectrum for users (simplicity, cheapness, reduction of waste, fastness, suitability for routine use, automatability etc.)

In addition, a further application of this variant is not only to extract nucleic acids in a reaction cavity but to allow also a subsequent target amplification and subsequent analysing in the same reaction vessel, if necessary, hybridisation reactions, if necessary, or sequencing on solid phases.

On this basis e.g. an 0.5 ml Eppendorf PCR vessel is modified by means of techniques known to experts by a negatively charged or potentially negative functional group. The photochemical coupling of an acetyl group, carboxyl group or hydroxyl group with the surface of the reaction vessel is e.g. suited for that. Then, the sample selected for isolating nucleic acids (e.g. whole blood) is put into the reaction vessel and incubated with a lysis buffer containing the antichaotropic salt fraction, with adding e.g. ammonium chloride, a detergent and a proteolytic enzyme and the vessel is incubated at 70° C. for 5 min.

To maximize the binding of nucleic acids a detergent/alcohol mixture may be still pipetted after completing the lysis of the starting material. Then, the batch is shortly incubated and subsequently poured off the reaction vessel. Now, the nucleic acid is bound to the functionalised surface of the reaction vessel and is subsequently shortly washed with an alcoholic wash buffer and the alcohol is removed by incubation,e.g. at 70° C. Further, the elution of the bound nucleic acids is effected in an expert way by adding a low salt buffer (e.g. 10 mM of tris-HCl) to the reaction vessel and a short incubation (e.g. 2 min.) at e.g. 70° C. Thus, the nucleic acid is available for subsequent use.

As has been shown, all reactions of isolating nucleic acid from a complex starting material proceed in one reaction vessel, i.e. the lysis of the starting material, binding of nucleic acids, washing of the bound nucleic acids and elution of the nucleic acids, are implemented in and with one reaction vessel.

The extraction kits of the Qiagen company at present most frequently applied worldwide need for lysing, binding, washing and elution always one filter cartridge and at least 4 separate reaction vessels, including, in addition, multiple centrifugation steps.

Contrary to this, the variant according to the invention allows to extract nucleic acid without a single centrifugation step. An enormous advantage relating to time may be also derived from this. These advantages relate also to the methods of nucleic acid extraction cited in U.S. Pat. No. 5,234,809 described by Boom.

But apart from the potential extraction of nucleic acid the bound nucleic acid may also remain at the surface of the described 0.5 ml reaction vessel and be e.g. subsequently directly used for a PCR application by adding a complete PCR mix (primer, nucleotide, polymerase buffer, Taq polymerase, magnesium), i.e. extraction and amplification proceed then in the same reaction vessel.

These examples illustrate the enormous advantages and the wide applicability derivable from the invention. In one variant it enables the whole process of preparation of samples via amplification and also analysing, if necessary, to proceed e.g. in one reaction cavity. Thus, with the provision of modified reaction vessels (or also other solid surfaces) and the appropriate lysis/binding buffers new standards are developed in laboratories dealing with molecular biology and primarily with nucleic acid diagnosing with the problems of contaminating samples which are sufficiently known being drastically reduced by the new potential solutions of application.

A further advantage and also a further application is that the nucleic acids fixed on the surface will remain stably fixed also at least for a longer time, thus being available for a later treatment, i.e. the PCR will not have to follow immediately after extraction. A further field of application is the fully automated extraction of nucleic acid and analysing, if necessary, using the surfaces bearing negative or potentially negative charges which are described here (preferably plastic surfaces of suitable reaction cavities, e.g. microtest plates).

The lysisibinding buffer systems according to the invention with antichaotropic salts as main components including a proteolytic enzyme, if necessary, may be also provided as a solid formulation. For this purpose the mixtures of salts and detergents, additives and enzymes, if necessary, will be aliquoted in usual reaction vessels and incubated for a few hours at 95° C. or lyophilysed according to methods known as such and thus converted into a solid formulation.

These solid formulations in complex ready reaction mixtures for isolating nucleic acids are stable in long-time storage, i.e. also the biological activity of the proteolytic enzyme component is maintained during long-time storage (see example of execution). Thereby, the stable formulation of lysis buffer mixtures is prepared without adding protective additives known as such, simply by a low-temperature lyophilisation.

All test kits for the extraction of nucleic acids offered commercially contain the required components individually, specific solutions have to be prepared only by the user. Apart from that, the stability of the solutions is restricted. A further drawback consists in the fact that the user has to consider multiple pipetting steps for various individual solutions while isolating nucleic acids using test kits customary at present. This increases the risk of contamination drastically, notably in the field of medical diagnostics. Furthermore, it is disadvantagous that e.g. owing to the limits of loading widely customary centrifugation columns which are mainly applied for isolating nucleic acids also the quantity of the starting material is strongly limited. This is due to the fact that lysis and binding buffers required for the extraction have still to be added to the starting material.

By providing a stable formulation as a lysis mix stable in storage on the basis of antichaotropic salts the existing problems are solved in a completely simple way. This formulation has the following advantages:

1. Long-time storage of lysis buffer mixes ready for use.
2. Stabilization of proteolytic enzymes in ready lysis mixtures and their long-time storage
3. Use of bigger quantities of starting materials at an equal dimensioning of existing centrifugation columns (e.g. triplication of the starting quantity)
4. Reduction of contamination risks by reducing pipetting steps and solutions
5. Uptake of sample in the ready lysis mix also outside the laboratory and its long-time storage, if necessary
6. Stable dispatch of samples and cooling.

The ready, solid, stable lysis buffer mixes consisting of a multitude of individual components including proteolytic enzymes, if necessary, are easily to handle (also by persons who do not have special knowledge) as the reaction is started simply by adding a sample containing the nucleic acid to be isolated. Apart from that, we can proceed on the fact that the mixtures have a life time of at least 6 months according to the substances they contain, thus a transport of the sample at room temperature is no longer a problem either.

The advantage of the solid formulations is based on the fact that the sample containing nucleic acids will be only put into the reaction vessel containing the lysis buffer stable in storage for the lysis of the nucleic acids contained in the sample materials and the sample is lysed in the respective reaction vessel, if necessary, by adding water. Costly multiple pipetting steps which burden contamination are completely dropped. The problems known which are connected with collecting and preparing clinical and forensic samples, given field conditions, are solved by the formulation according to the invention and a formulation easily to handle is available.

To our surprise, the practical application showed also that after adding the starting material to be lysed, if necessary, when adding a solid sample after adding $H_2O$ the solid formulation may be again converted to a liquid phase without causing problems, given standard reaction conditions.

To sum up there is to be stated:

The subject of the invention is the use of antichaotropic salts in formulations which do not contain chaotropic components for isolating nucleic acids with binding to a solid phase, in particular DNA of optional complex starting materials. The formulations contain lysis/binding buffer systems which have at least one antichaotropic salt component, a solid phase and wash and elution buffers known as such.

The lysis/binding buffer system may be available as an aqueous solution or as a solid formulation in reaction vessels ready for use.

All carriers may serve as solid phase used for isolating chaotropic reagents, preferably glass fiber mats, glass membranes, silicon carriers and aerosiles or carriers which have a negatively charged surface or chemically modified surfaces showing a negative charge potential.

Furthermore, the subject of the invention is a method for isolating nucleic acids, in particular DNA, from optional complex starting materials, using the formulations mentioned which is characterized by a lysis of the starting material, binding nucleic acids to a carrier, washing the nucleic acids bound to the carrier and elution of the nucleic acids.

Owing to the DNA quality achieved it is also well suited for the preparative isolation and purification of DNA for use in gene therapy.

The subject of the invention are also solid formulations of lysis buffer systems stable in storage and ready for use for isolating nucleic acid on the basis of antichaotropic salts available as mixes ready for use in conventional reaction vessels. The solid formulations of the lysis buffer batches are activated by adding only the sample (in the case of liquid samples such as e.g. whole blood, saliva, cell suspensions, serum, plasma, liquor), in the case of solid starting materials such as tissue, hair roots, blood stains on solid surfaces, cigarette butts, deparaffined tissue etc. additionally by adding water and carry out the lysis of the starting materials. After completing the lysis of the starting material the lysis batch is incubated in the way known as such, if necessary, after adding an ethanolic solution or an alcohol/detergent mixture with the various solid phases binding nucleic acid (suspension, centrifugation column) being used. The subsequent binding of the nucleic acids on the respective solid phases, washing of the bound nucleic acids and the final elution will be effected as has been already described according to the state of the art.

By these solid formulations novel solutions are given, primarily for optional fields of application of nucleic acid diagnostics.

There should be once more pointed out that the invention variant as a one-step method and a "single tube" method allows to isolate nucleic acids from complex starting materials, if necessary, target amplifications and, if necessary, a subsequent analysing of the amplified nucleic acid section. Thereby, the starting material need not be a nucleic acid already isolated but the complex starting material containing the nucleic acid. The surface required for binding the nucleic acid contains negative or potentially negative functional groups. Binding of the nucleic acid is implemented in a lysis/binding buffer with the ions required for binding the negatively charged nucleic acid to the negatively functionalised surface coming from antichaotropic salts.

Thus, there are implementable:

1. a "single tube" method for isolating nucleic acids from complex starting materials
2. a "single tube" method for isolating nucleic acids and subsequent target multiplication
3. a "single tube" method for isolating nucleic acids from complex starting materials, subsequent target multiplication and subsequent analysing of the multiplied nucleic acid section.

This means the isolation of nucleic acids from most various starting materials containing DNA and if necessary, target multiplication and analysing, take place in the very same reaction cavity or, if necessary, on one and the same reaction surface.

The formulations according to the invention and the universal method of binding nucleic acids to solid phases for the isolation, purification and subsequent complex molecular analysis of nucleic acids from optional starting materials and quantities containing nucleic acids represent a novel platform technology for the development of integral fully automated systems of gene analytics which allow to prepare the sample, multiply and analyse the target in one reaction cavity.

Hereinafter, the invention is explained in greater detail by means of examples of execution.

1. Isolation of Genomic DNA From Various Plant Materials

Always 50–100 mg of the starting plant material were comminuted with a mortar under liquid nitrogen and subsequently transferred to a 1.5 ml Eppendorf reaction vessel.

Adding of 500 µl of lysis buffer (2% CTAB, 2% polyvinyl pyrrolidone, 10 mM of tris-HCl, 20 mM of EDTA and 1.3 M of ammonium chloride) and incubation at 65° C. for at least 30 mm.

Centrifugating of unlysed components and mixing of the supernatant liquid with 200 µl of isopropanol.

Transfer of the solution to a centrifugation column with a glass fiber membrane (micro spin column, company LIDA).

Centrifugation at 12.000 rpm for 2 min. Discarding of the filtrate and washing of the membrane two times with a wash buffer (50 mM of NaCl; 10 mM of tris-HCl; 1 mM of EDTA; 70% v/v ethanol).

After removing ethanol in a short centrifugation step (12,000 rpm for 2 min.) adding of 200 µl of elution buffer (10 mM of tris-HCl, pH 8.7) and elution of DNA by centrifugation at 10,000 rpm for 1 min.

Always 20 μl of the eluted DNA were put onto an agarose gel and represented after coloring with ethidium bromide (FIG. 1).

2. Simultaneous Isolation of Genomic DNA From Various Starting Materials with a Universal Buffer System The following samples were used for isolation:

1-whole blood frozen: 50 ml, 2-whole blood: 100 μl, 3-cucumber: 50 mg; 4-tomato plant leaf: 100 mg; 5-saliva sample: 100 μl; 6-chicken liver; foodstuffs frozen: 5 mg; 7-chicken liver; foodstuffs frozen: 20 mg; 8-hair root, 9-turkey salami: 50 mg; 10-yew, needles: 100 mg.

All samples were incubated in 500 μl of lysis buffer (2% CTAB; 2% polyvinyl pyrrolidone, 10 mM of tris-HCL; 20 mM of EDTA and 1.5 M of ammonium chloride) and with the exception of all plant samples with adding 20 μl of proteinase K (20 mg/ml) at 65° C. Subsequently 200 μl of isopropanol were added to the lysates and transferred to a centrifugation column with a glass fiber membrane (micro spin column; company LIDA). Centrifugation at 12,000 rpm for 2 min. Discarding of the filtrate and washing of the membrane twice with a wash buffer (50 mM of NaCl; 10 mM of tris-HCl; 1 mM of EDTA; 70% v/v ethanol). After removing ethanol in a short centrifugation step (12,000 rpm for 2 min.) adding of 50–200 μl of elution buffer (10 mM of tris-HCl, pH 8.7) and elution of DNA by centrifugation at 10,000 rpm for 1 min.

Figure 2:

Always ⅕ of the eluted DNA were loaded onto an agarose gel and represented after coloring with ethidium bromide (FIG. 2).

3. Isolation of Genomic DNA From Swabs of the Oral Mucosa

The isolation of DNA from swabs of the oral mucosa is described hereinafter.

Always 400 μl of lysis buffer (CTAB, polyvinyl pyrrolidone, ammonium chloride, tris, EDTA) were transferred to a 1.5 ml Eppendorf reaction vessel. The swab material was squeezed out and 20 μl of proteinase K (20 mg/ml) were added to the suspension. Subsequently the batch was incubated at 70° C. for 10 min. After lysing 200 μl of a detergent/isopropanol mixture were added, the sample was shaken shortly, subsequently transferred to a commercially available centrifugation column (company LIDA; glass fiber membrane) and centrifuged at 12,000 rpm for 1 min.

Figure 3:
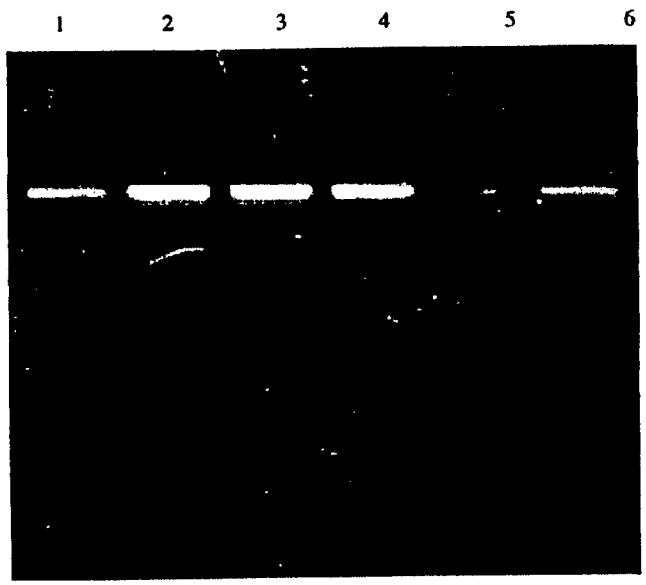

Then the column was washed twice with a wash buffer (NaCl, tris-HCl, EDTA, ethanol) containing ethanol (centrifugation at 12,000 rpm; 1 min.) and the membrane was dried in a short centrifugation step. By adding 200 μl of elution buffer (10 mM of tris-HCl) the bound DNA was eluted from the filter membrane in a short centrifugation step (10,000 rpm; 1 min.) Always 20 μl of the DNA isolated from the two extraction processes were placed on 0.7% TAE agarose gel for analysing and analysed after coloring with ethidium bromide (FIG. 3).

4. Comparison of the Extraction of DNA From Whole Blood Samples (200 μl) According to the Invention with a Commercial Kit on the Basis of Binding Nucleic Acids in the Presence of Chaotropic Salts The isolation of genomic DNA by means of the method according to the invention was compared with a commercially available and traditionally applied method for isolating genomic DNA with using chaotropic salts for binding nucleic acids. The extraction of genomic DNA by means of the comparative method was carried out on the basis of the regulation governing application.

The isolation of DNA by means of the method according to the invention is described hereinafter.

Always 200 μl of a whole blood sample (treated with EDTA, fresh) were transferred to a 1.5 ml Eppendorf reaction vessel.

After adding 350 μl of a lysis buffer (CTAB, polyvinyl pyrrolidone, ammonium chloride, tris, EDTA) and 20 μl of proteinase k (20 mg/ml) an incubation was carried out at 70° C. for 10 min. for lysing the starting material.

After lysing 180 μl of a detergent/isopropanol mixture was added, the sample was shortly shaken, subsequently transferred to a commercially available centrifugation column (company LIDA; glass fiber membrane) and centrifuged at 12,000 rpm for 2 min.

Then, the column was washed twice with a wash buffer containing ethanol (NaCl, tris-HCl, EDTA, ethanol) (centrifugation at 12,000 rpm; 1 min.) and the membrane was dried in a short centrifugation step. By adding 200 μl of elution buffer (10 mM tris-HCl) the bound DNA was eluted from the filter membrane in a short centrifugation step (10,000 rpm, 1 min.).

Always 10 μl of the DNA isolated from the two extraction processes were put onto a 0.7% TAE agarose gel and analysed after coloring with ethidium bromide.

Figure 4:
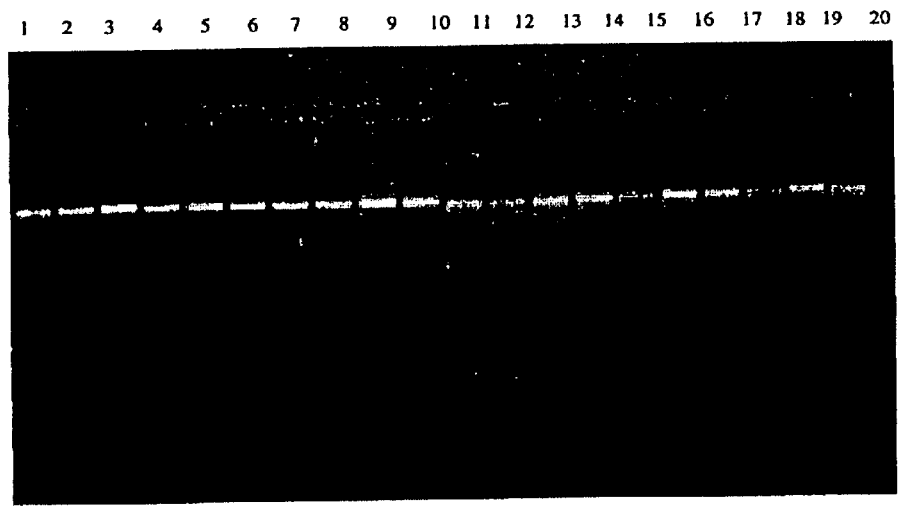

The yields of genomic DNA, their integrity (clean individual bands without low-molecular smear bands) and the reproducibility of the extraction methods were compared. As can be seen by means of the method according to the invention better results can be achieved than by means of the comparative method (FIG. 4).

5. Comparison of the Extraction of DNA from Whole Blood Samples (5 μl) According to the Invention by Means of a Commercial Kit on the Basis of Binding Nucleic Acids in the Presence of Chaotropic Salts The isolation of genomic DNA by means of the method according to the invention was compared with the isolation of genomic DNA according to a commercially available and traditionally applied method with using chaotropic salts for binding nucleic acid. Genomic DNA were extracted according to the comparative method on the basis of the regulation governing application.

The isolation of DNA by means of the method according to the invention is described hereinafter.

Always 5 μl of a whole blood sample (treated with EDTA; fresh) were transferred to a 1.5 ml Eppendorf reaction vessel.

The sample was filled up to a volume of 200 μl by adding 195 μl of 1×PBS buffer and after adding 350 μl of a lysis buffer (CTAB, polyvinyl pyrrolidone, ammonium chloride, tris, EDTA) and 20 μl of proteinase K (20 mg/ml) an incubation was carried out at 70° C. for 10 min. for lysing the starting material.

After lysing 180 μl of a detergent/isopropanol mixture were added, the sample was shortly shaken, subsequently transferred onto a commercially available centrifugation column (company LIDA, glass fiber membrane) and centrifuged at 12,000 rpm for 2 min.

Then the column was washed twice with a wash buffer (NaCl, tris-HCl, EDTA, ethanol) (centrifugation at 12,000 rpm; 1 min.) and the membrane was dried in a short centrifugation step. By adding 200 μl of elution buffer (10 mM of tris-HCl) the bound DNA was eluted from the filter membrane in a short centrifugation step (10,000 rpm, 1 min.).

Always 20 μl of the DNA isolated from the two extraction processes were put onto a 0.7% TAE agarose gel and analysed after coloring with ethidium bromide.

Figure 5:
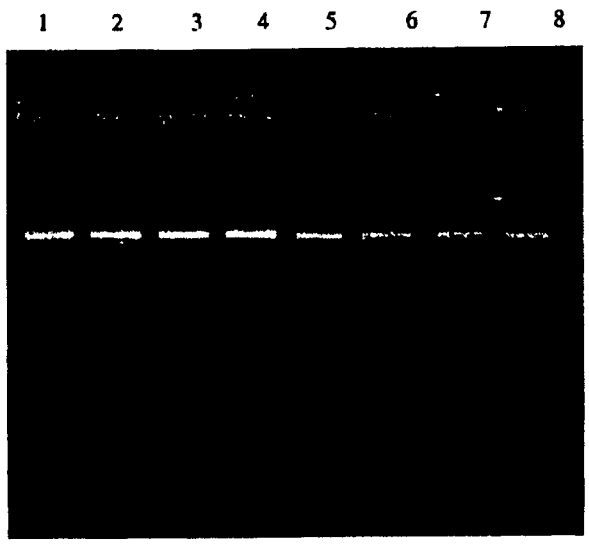

The possibility of isolating genomic DNA from very small quantities of starting material and the reproducibility of the extraction processes were detected and compared. As can be seen by means of the method according to the invention better results can be achieved than by means of the comparative method (FIG. 5).

6. Comparison of the Extraction of DNA According to the Invention From Various Types of Animal Tissue Samples and Various Quantities of Starting Material by Means of a Commercial Kit on the Basis of Binding Nucleic Acids in the Presence of Chaotropic Salts The isolation of genomic DNA by means of the method according to the invention was compared with the isolation of genomic DNA according to a commercially available and traditionally applied method with using chaotropic salts for binding nucleic acid. Genomic DNA was extracted according to the comparative method on the basis of the regulation governing application.

The isolation of DNA by means of the method according to the invention is described hereinafter.

Always 5 mg or 20 mg of tissue samples of pork kidney, pork heart and pork liver were transferred to a 1.5 ml Eppendorf reaction vessel. 400 µl of a lysis buffer (CTAB, polyvinyl pyrrolidone, ammonium chloride, tris, EDTA) and 40 µl of proteinase K (20 mg/ml) were added to the sample.

The lysis of the starting material was carried out through incubation at 52° C.

After the lysis components not lysed were centrifuged off in a short centrifugation step (14,000 rpm, 1 min.) and the supernatant liquid was added to a new reaction vessel with 200 µl of a detergent/isopropanol mixture, the sample was shortly shaken, subsequently transferred to a commercially available centrifugation column (company LIDA, glass fiber membrane) and centrifuged at 12,000 rpm for 2 min.

The column was then washed twice with a wash buffer containing ethanol (NaCl, tris-HCl, EDTA; ethanol) (centrifugation at 12,000 rpm; 1 min.) and the membrane was dried in a short centrifugation step. By adding 200 µl of elution buffer (10 mM of tris-HCl) the bound DNA was eluted from the filter membrane in a short centrifugation step (10,000 rpm., 1 min.).

Always 10 µl of the DNA isolated from the two extraction processes were put onto a 0.7% TAE agarose gel and analysed after coloring with ethidium bromide.

The possibility of isolating genomic DNA from various tissue samples and various quantities of starting material as regards the yields of genomic DNA, their integrity (clean individual bands without low-molecular smear bands) and the reproducibility of the extractions were detected and compared.

As can be seen, by means of the method according to the invention better results can be achieved than by means of the comparative method (FIG. 6).

7. Extraction of DNA From Whole Blood Samples (200 µl) by Means of the Method According to the Invention and Binding of Nucleic Acids to Various Carriers Used for Binding with Chaotropic Salts Being Mediators The isolation of genomic DNA from 200 µl of whole blood by means of the method according to the invention and binding of the nucleic acids to various carriers (column membranes and suspensions) used for isolating nucleic acids by means of chaotropic agents are represented.

The extraction of DNA is carried out as described in example 4 with various carriers having been used instead of the glass fiber membrane of company LIDA.

Always 20 µl of the isolated DNA were put onto a 0.7% TAE agarose gel and analysed after coloring with ethidium bromide.

As is to be seen in FIG. 7, the method according to the invention implements the binding of the nucleic acids to various carriers used in the chaotropic methods which have been known so far.

8. Preparation of a Lysis Buffer System Stable in Storage Including a Proteolytic Enzyme (Buffer Mix 1) and Use of the Lysis Buffer System for Isolating Genomic DNA From Various Starting Materials Preparation of a lysis buffer stock solution containing 3 M of potassium chloride, 2% CTAB, 18.2 mM of tris-HCl (pH 8.3), 12.5 mM of EDTA, 2.8% polyvinyl pyrrolidone. Aliquoting of always 400 µl of stock solution in 1.5 ml Eppendorf reaction vessels and adding of 40 µl of proteinase K (20 mg/ml).

Lyophilisation of lysis buffer mixtures in a lyophilisation plant (alpha 2; company Christ). Subsequent storage of the lysis buffer mixtures in closed reaction vessels at room temperature for 6 months.

The extraction of the genomic DNA was carried out from:
A: 500 µl of whole blood
B: 400 µl of salivary sample
C: deparaffined tissue material 1. Extraction of DNA from Whole Blood Adding of 500 µl of whole blood to the solid formulation of the lysis buffer and incubation at 70° C. for 10 min. Adding of 200 µl of isopropanol and transfer of the suspension to a centrifugation column (glass fiber mat).

Centrifugation at maximum speed for 2 min. and discarding of the centrifugate.

Adding of 600 µl of a wash buffer (70% ethanol, NaCl, tris, EDTA), centrifugation at maximum speed for 1 min. and discarding of the centrifugate. Repetition of the washing step. Subsequently drying of the membrane by centrifugation at maximum speed for 2 min. Elution of DNA from the membrane by adding 200 µl of an elution buffer (70° C.) and centrifugation at maximum speed for 1 min.

2. Extraction of DNA from Salivary Samples

Adding of 500 µl of salivary sample to the solid formulation of the lysis buffer and incubation at 70° C. for 10 min. Adding of 200 µl of isopropanol and transfer of the suspension to a centrifugation column (glass fiber mat).

Centrifugation at maximum speed for 2 min. and discarding of the centrifugate. Adding of 600 µl of a wash buffer (70% ethanol, NaCl, tris, EDTA), centrifugation at maximum speed for 1 min. and discarding of the centrifugate. Repetition of the washing step. Subsequently drying of the membrane by centrifugation at maximum speed for 2 min.

Elution of DNA from the membrane by adding 200 µl of an elution buffer (70° C.) and centrifugation at maximum speed for 1 min.

3. Extraction of DNA from Deparaffined Tissue

Adding of the deparaffined tissue piece to the solid formulation of the lysis buffer. Adding of 500 µl of dd $H_2O$ and incubation at 52° C. for 30 min.

Adding of 200 µl of isopropanol and transfer of the suspension to a centrifugation column (glass fiber mat).

Centrifugation at maximum speed for 2 min. and discarding of the centrifugate. Adding of 600 µl of a wash buffer (70% ethanol, NaCl, tris, EDTA), centrifugation at maximum speed for 1 min and discarding of the centrifugate. Repetition of the washing step. Subsequently drying of the membrane by centrifugation at maximum speed for 2 min.

Elution of DNA from the membrane by adding 200 µl of an elution buffer (70° C.) and centrifugation at maximum speed for 1 min.

Figure 8:
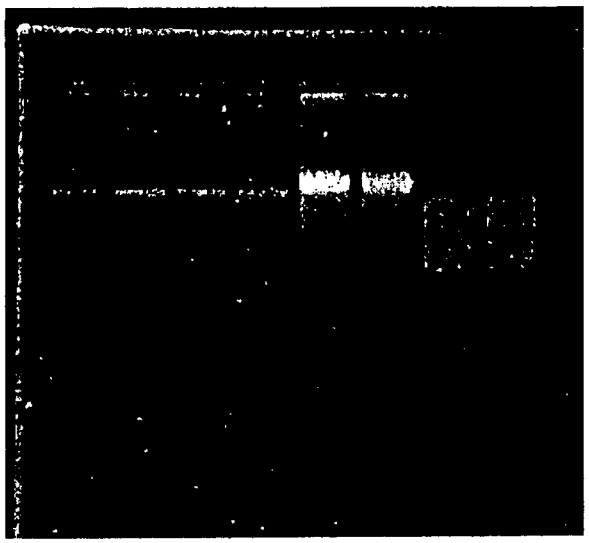

Subsequently the extracted DNA was gel electrophoretically analysed. For this purpose, always 1/10 of the whole DNA eluate were applied (FIG. 8).

9. Preparation of a Lysis Buffer System Stable in Storage Including Proteinase K (Buffer Mix 2) and Use of the Lysis Buffer System for Isolating Genomic DNA From 8 Individual Whole Blood Samples (100 μl)

Preparation of a lysis buffer stock solution containing 3 M of ammonium chloride, 2% polyvinyl pyrrolidone, 16.7 mM of EDTA, 60 mM of tris-HCl, 1.6% CTAB, 20 μl of proteinase K (20 mg/ml).

Figure 9:
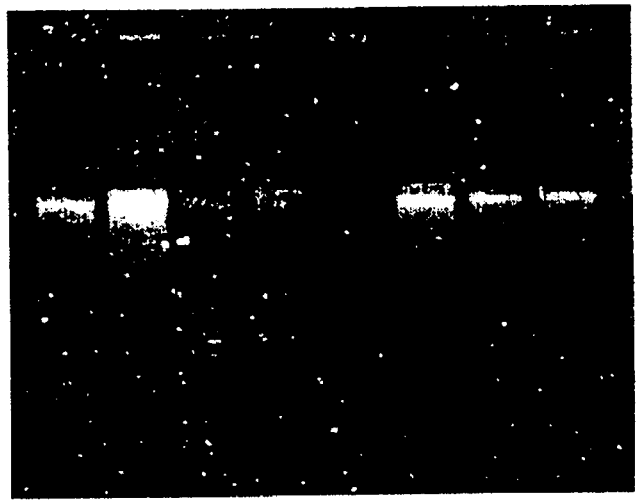

Aliquoting of always 400 μl of the stock solution in 1.5 ml Eppendorf reaction vessels and incubation of the open Eppendorf reaction vessels in a thermomixer at 95° C. up to its complete drying up. Subsequently closing of the reaction vessels and storage at room temperature for 12 months.
Extraction of DNA from whole blood Adding of 100 μl of whole blood to the solid formulation of the lysis buffer and incubation at 70° C. for 10 min. Adding of 20 μl of a mineral carrier suspension on silica basis and short mixing. Incubation of the batch for 1 min. Pelleting of the carrier by short centrifugation. Washing of the carrier pellets with 800 μl of a wash buffer (70% ethanol, NaCl, tris, EDTA) and subsequent removal of the remaining ethanol by incubation at 70° C. Elution of DNA from the carrier by adding 200 μl of an elution buffer heated to 70° C. (10 mM of tris-HCl; pH 8.69 and separation of the nucleic acid from the carrier by centrifugation at maximum speed for 1 min. and transfer of the nucleic acid to a new reaction vessel. The extracted DNA was subsequently gel electrophoretically analysed. For this purpose, always 1/10 of the whole DNA eluate were applied (FIG. 9).

10. Isolation of Genomic DNA From Peripheral Blood Lymphocytes by a Direct Binding to the Functionalised Surfaces of a Microtest Plate A commercially available plate with a COO⁻ group coating was used as microtest plate. Always one strip of the plate (8 wells) with functional groups and one strip without COO⁻ groups as a negative control were used for the isolation.

All wells were loaded with 30 μl of peripheral blood lymphocytes in 1×PBS buffer and 180 μl of a lysis buffer (ammonium chloride, CTAB, polyvinyl pyrrolidone, tris-HCl, EDTA, proteinase K) were added and incubated at 70° C. for 5 min. Subsequently 80 μl of a detergent/isopropanol mixture were added. The batches were shortly shaken and incubated for 5 min. Subsequently the solutions were poured off the wells. Thereupon, each of the wells was washed twice with a wash buffer containing ethanol and the remaining ethanol was removed at 70° C. by a short incubation.

The elution of the nucleic acids was carried out by adding 25 μl 10 mM of tris-HCl and an incubation for 2 min.

Figure 10:
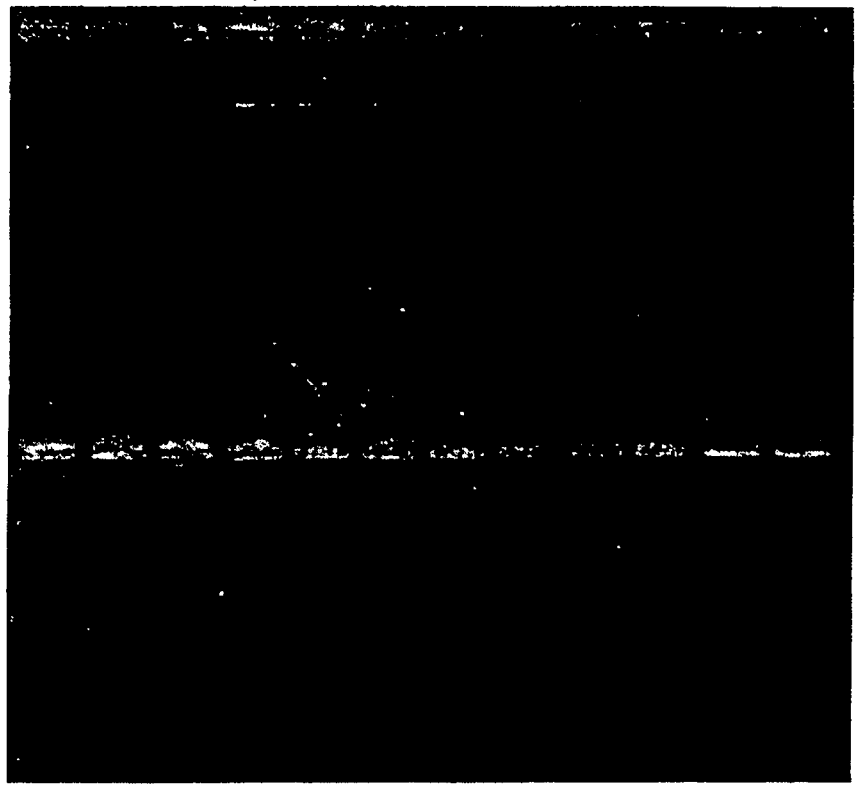

Thereupon, the eluates were evaluated on a 0.7% agarose gel (FIG. 10).

FIG. 1
Traces:
1—onion (fresh);
2—chive (fresh, green)
3—chive (fresh; green)
4—geranium (hanging; flowers and leaves; fish)
5—geranium (standing; leaves; fresh)
6—yew (needles; fresh)
7—mousetail grass (fresh; leaves; green)
8—common tansy (fresh green, leaves)
FIG. 2
Traces:
1—whole blood, frozen; 50 μl
2—whole blood, 100 μl,
3—cucumber; 50 mg
4—tomato plant leaf; 100 mg;
5—saliva sample; 100 μl;
6—chicken liver, foodstuffs frozen; 5 mg;
7—chicken liver, foodstuffs frozen; 20 mg;
8—hair roots,
9—turkey salami; 50 mg
10—yew, needles, 100 mg
FIG. 3
Traces 1–6: DNA from swab samples of oral mucosa
FIG. 4
Traces:
1–10: Extraction method according to the invention
11–20: Comparative method
FIG. 5:
Traces:
1–4: Extraction method according to the invention
5–8: Comparative method
FIG. 6
Traces
1: Extraction method according to the invention; 5 mg kidney
2: Comparative method; 5 mg kidney
3: Extraction method according to the invention; 20 mg kidney
4: Comparative method: 20 mg kidney
5: Extraction method according to the invention; 5 mg heart
6: Comparative method; 5 mg heart
7: Extraction method according to the invention; 20 mg heart
8: Comparative method; 20 mg heart
9: Extraction method according to the invention; 5 mg liver
10: Comparative method; 5 mg liver
11: Extraction method according to the invention; 20 mg liver
12: Comparative method; 20 mg liver
FIG. 7
Traces:
1/2: Membrane supplier A (commercially available extraction kit)
3/4: Membrane supplier B (commercially available extraction kit)
5/6: Membrane supplier C (commercially available extraction kit)
7/8: Carrier suspension of silicon oxide
9/10: Carrier suspension of diatom earth
11/12: Carrier suspension of aerosiles (200 m²/g)
FIG. 8
Traces:
1–4: DNA extracted From saliva samples
5–6: DNA extracted from whole blood
7–8: DNA extracted from deparaffined tissue material
FIG. 9
FIG. 10
COO⁻ microtest plate strips
unmodified microtest plate strip

What is claimed is:

1. A kit for isolating nucleic acids in the absence of a chaotropic salt, wherein one or more nucleic acids bind to a substrate, the kit comprising:
   a) a lysis/buffer system comprising at least one antichaotropic salt at a concentration that allows binding of said one or more nucleic acids to said substrate,
   b) said substrate, and
   c) optionally, one or more detergents and/or other additives;
   wherein all carriers having a negatively functionalized surface(s) which may be converted to a negative charge potential, serve as the substrate means and wherein the surface of the substrate is modified by at least one chosen from the group consisting of an acetyl group, carboxyl group and hydroxyl group.

2. The kit according to claim 1, wherein at least one protein-degrading enzyme proteinase K is included in the lysis/buffer system.

3. The kit according to claim 1, further comprising a wash buffer having an alcohol.

4. The kit according to claim 3, wherein the wash buffer comprises ethanol at a concentration effective to retain the nucleic acids bound to the column during washing.

5. The kit according to claim 3, wherein the wash buffer comprises at least about 50% ethanol.

6. The kit according to claim 1, wherein the nucleic acid is DNA.

7. The kit according to claim 1, wherein the nucleic acid is RNA.

8. The kit according to claim 1, wherein the antichaotropic component is a salt chosen from the group consisting of ammonium, cesium, sodium and potassium.

9. The kit according to claim 1, wherein the lysis/buffer system contains detergents and additives.

10. The kit according to claim 9, wherein the detergents and additives are chosen from the group consisting of of tris-HCl, EDTA, polyvinyl pyrolidone, CTAB (hexadecyltrimethylammonium bromide), Triton X-100, Nonidet-P40, n-lauryl sarcosine, n-dodecylsulfate, sodium citrate, DU, Brij, Tween.

11. The kit according to claim 1, wherein the lysis/buffer system contains an alcohol for binding to the substrate.

12. The kit according to claim 1, wherein the lysis/buffer system is an aqueous solution.

13. The kit according to claim 1, wherein the lysis/buffer system is stable in storage in reaction vessels.

14. The kit according to claim 1, the substrate is chosen from the group consisting of chaotropic reagents, glass fiber mats, glass membranes, glasses, zeolites, ceramics, end silica carriers.

15. The kit according to claim 1, wherein the lysis/binding buffer system contains at least one enzyme.

16. The kit according to claim 1, wherein the complex starting material is chosen from the group consisting of compact plant materials, whole blood, tissue, microbioptate, paraffinne-coated materials, ercp-samples, swabs, foodstuffs, hair roots, cigarette butts, and food stains.

17. The kit according to claim 1, wherein the elution buffer comprises tris-HCl, TE, and water.

* * * * *